United States Patent
Kim et al.

(10) Patent No.: US 10,835,782 B2
(45) Date of Patent: Nov. 17, 2020

(54) ELECTRONIC DEVICE, SYSTEM, AND METHOD FOR DETERMINING SUITABLE WORKOUT IN CONSIDERATION OF CONTEXT

(71) Applicant: SAMSUNG ELECTRONICS CO., LTD., Suwon-si (KR)

(72) Inventors: Jaewon Kim, Seoul (KR); Jinyung Jung, Seoul (KR); Kyunghoon Han, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 170 days.

(21) Appl. No.: 15/609,326

(22) Filed: May 31, 2017

(65) Prior Publication Data

US 2017/0348563 A1 Dec. 7, 2017

(30) Foreign Application Priority Data

Jun. 1, 2016 (KR) .................. 10-2016-0068199

(51) Int. Cl.
*G09B 19/00* (2006.01)
*A63B 24/00* (2006.01)
(Continued)

(52) U.S. Cl.
CPC ........ *A63B 24/0075* (2013.01); *A61B 5/1118* (2013.01); *A61B 5/681* (2013.01);
(Continued)

(58) Field of Classification Search
CPC .......... A63B 24/0075; A63B 24/00878; G16H 20/30
See application file for complete search history.

(56) References Cited

U.S. PATENT DOCUMENTS 5,890,997 A * 4/1999 Roth ...................... A63B 71/06
482/8
9,465,893 B2 * 10/2016 Cheung ............... G06F 19/3481
(Continued)

FOREIGN PATENT DOCUMENTS

JP 2011-000191 1/2011
KR 10-2016-0001958 1/2016

OTHER PUBLICATIONS

Healthwise Staff; Physical Activity Helps Prevent a Heart Attack and Stroke; May 14, 2015; University of Michigan Health System; https://web.archive.org/web/20150923231018/https://www.uofmhealth.org/health-library/hw114892; (Year: 2015).*

*Primary Examiner* — Robert J Utama
(74) *Attorney, Agent, or Firm* — Nixon & Vanderhye P.C.

(57) ABSTRACT

An electronic device, a system, and a method for determining a suitable workout in consideration of a context are provided. The electronic device includes a communication module comprising communication circuitry configured to communicate with at least one other electronic device; a display configured to provide a user interface; a memory configured to store instructions therein; and a processor electrically connected to the communication module, the display, and the instructions stored in the memory, when executed by the processor, cause the processor to receive a command for executing a workout program, to collect context data for a user, and to determine whether it is suitable for the user to perform planned workout content based on the collected context data.

9 Claims, 17 Drawing Sheets

(51) Int. Cl.

| | | |
|---|---|---|
| *H04W 4/38* | (2018.01) | |
| *A61B 5/00* | (2006.01) | |
| *A61B 5/11* | (2006.01) | |
| *G09B 5/02* | (2006.01) | |
| *H04B 1/3827* | (2015.01) | |
| *H04L 29/08* | (2006.01) | |

(52) U.S. Cl.
CPC ............ *A63B 24/0087* (2013.01); *G09B 5/02* (2013.01); *G09B 19/003* (2013.01); *G09B 19/0038* (2013.01); *H04B 1/385* (2013.01); *H04L 67/12* (2013.01); *H04W 4/38* (2018.02)

(56) References Cited

U.S. PATENT DOCUMENTS

| | | | | |
|---|---|---|---|---|
| 9,665,873 | B2* | 5/2017 | Ackland | A63B 24/0075 |
| 2005/0070809 | A1* | 3/2005 | Acres | A61B 5/0006 |
| | | | | 600/508 |
| 2005/0234308 | A1* | 10/2005 | Naukkarinen | A61B 5/0537 |
| | | | | 600/300 |
| 2006/0184427 | A1* | 8/2006 | Singh | G06Q 30/00 |
| | | | | 705/26.1 |
| 2006/0228681 | A1* | 10/2006 | Clarke | A63B 24/00 |
| | | | | 434/236 |
| 2006/0264299 | A1* | 11/2006 | Farinelli | A63B 23/0211 |
| | | | | 482/8 |
| 2007/0005395 | A1* | 1/2007 | Singh | G06Q 50/22 |
| | | | | 705/2 |
| 2007/0179816 | A1* | 8/2007 | Lemme | A63B 24/0003 |
| | | | | 705/3 |
| 2007/0249468 | A1* | 10/2007 | Chen | A63B 24/00 |
| | | | | 482/8 |
| 2008/0077620 | A1* | 3/2008 | Gilley | G06F 19/3418 |
| 2008/0086318 | A1* | 4/2008 | Gilley | G06Q 10/06 |
| | | | | 705/319 |
| 2008/0096726 | A1* | 4/2008 | Riley | A63B 24/0006 |
| | | | | 482/8 |
| 2008/0103023 | A1* | 5/2008 | Chung | G11B 27/034 |
| | | | | 482/3 |
| 2010/0267520 | A1* | 10/2010 | Jang | A63B 24/00 |
| | | | | 482/8 |
| 2011/0009240 | A1* | 1/2011 | Chiu | A63B 24/0075 |
| | | | | 482/5 |
| 2011/0098928 | A1* | 4/2011 | Hoffman | A63B 24/0062 |
| | | | | 702/5 |
| 2012/0015779 | A1* | 1/2012 | Powch | A61B 5/02055 |
| | | | | 482/9 |
| 2012/0040799 | A1* | 2/2012 | Jaquish | A63B 21/00047 |
| | | | | 482/9 |
| 2013/0172764 | A1* | 7/2013 | Buckley | A61B 5/0205 |
| | | | | 600/509 |
| 2014/0065587 | A1* | 3/2014 | Liebhart | G06F 19/3481 |
| | | | | 434/247 |
| 2014/0073486 | A1* | 3/2014 | Ahmed | A61B 5/02405 |
| | | | | 482/9 |
| 2014/0172362 | A1 | 6/2014 | Burton et al. | |
| 2015/0066683 | A1* | 3/2015 | Azose | G06Q 30/0631 |
| | | | | 705/26.7 |
| 2015/0224364 | A1* | 8/2015 | Hsieh | A63B 24/0087 |
| | | | | 700/275 |
| 2015/0360083 | A1* | 12/2015 | Lagree | A63B 24/0075 |
| | | | | 482/130 |
| 2016/0263439 | A1* | 9/2016 | Ackland | A61B 5/021 |
| 2017/0039480 | A1* | 2/2017 | Bitran | G06F 19/3481 |
| 2017/0063475 | A1* | 3/2017 | Feng | A61B 5/1123 |
| 2017/0164891 | A1* | 6/2017 | Wang | A61B 90/98 |
| 2017/0165523 | A1* | 6/2017 | Chou | A61B 5/6895 |
| 2017/0216671 | A1* | 8/2017 | Wisbey | A63B 24/0075 |
| 2017/0360356 | A1* | 12/2017 | Ashdown | A61B 5/0022 |

* cited by examiner

FIG. 12A
2: 24 pm
Not good for Run
Why not
Stretch at home?
30 mins
Start

ELECTRONIC DEVICE, SYSTEM, AND METHOD FOR DETERMINING SUITABLE WORKOUT IN CONSIDERATION OF CONTEXT

CROSS-REFERENCE TO RELATED APPLICATION

This application is based on and claims priority under 35 U.S.C. § 119 to Korean Patent Application No. 10-2016-0068199 filed on Jun. 1, 2016, in the Korean Intellectual Property Office, the content of which is incorporated by reference herein in its entirety.

BACKGROUND

Field of the Disclosure

The present disclosure relates generally to an electronic device, a system, and a method for determining a suitable workout in consideration of a context. For example, the present disclosure relates to an electronic device, a system, and a method for providing a suitable workout to a user using various contexts related to the user.

Description of Related Art

Recently, as people are increasingly concerned about healthcare and fitness, various devices for more scientific workout and body (health) care, in particular, for weight loss treatments, have been provided. For example, wearable devices that can be conveniently worn on the body to measure an exercise amount for exercise treatments have been provided.

A wearable device may refer, for example, to a device that can be attached to a user's body to perform a computing action. For example, a wearable device may be implemented in various types that can be attached to the user's body, such as, a watch, glasses, a bracelet, a ring, a necklace, shoes, and a sticker.

As an example, wearable devices have been implemented in an arm band type that is worn on a user's inner forearm to measure a heart rate through an optical sensor and in a ring type that is worn on a user's finger to measure a heart rate through an optical sensor.

Various types of wearable devices may measure bio-signals of users who wear the wearable devices, or may collect workout data.

However, since such wearable devices do not consider various contexts, they may cause users to perform unreasonably planned workouts and thus may be unable to prevent bad influences from being exerted on the health.

SUMMARY

An example aspect of the present disclosure provides an electronic device, a system, and a method capable of determining a workout that is suitable for the current context in consideration of various pieces of context data, such as user-based context data, environment-based context data, and reference-based context data.

In accordance with an example aspect of the present disclosure, an electronic device includes a communication module comprising communication circuitry configured to communicate with at least one other electronic device; a display configured to provide a user interface; a memory configured to store instructions therein; and a processor electrically connected to the communication module, the display, and the memory, wherein the instructions stored in the memory, when executed by the processor, cause the processor to receive a command for executing a workout program, to collect context data for a user, and to determine whether it is suitable for the user to perform planned workout content based on the collected context data.

In accordance with another example aspect of the present disclosure, a wearable device includes a communication module comprising communication circuitry configured to communicate with at least one other electronic device; a display configured to provide a user interface; a sensor module comprising at least one sensor configured to measure a bio-signal; a memory configured to store instructions therein; and a processor electrically connected to the communication module, the display, the sensor module, and the memory, wherein the instructions stored in the memory, when executed by the processor, cause the processor to receive a command for executing a workout program, to collect context data for a user, to control the sensor module to measure a bio-signal of the user, and to determine whether it is suitable for the user to perform planned workout content based on the collected context data and the measured bio-signal.

In accordance with still another example aspect of the present disclosure, a method for determining a suitable workout in consideration of a context includes receiving a command for executing a workout program, collecting context data for a user, and determining whether it is suitable that the user performs planned workout content based on the collected context data.

In accordance with still another example aspect of the present disclosure, a method for determining a suitable workout in consideration of a context includes receiving a command for executing a workout program, collecting context data for a user, measuring a bio-signal of the user, and determining whether it is suitable that the user performs planned workout content based on the collected context data and the measured bio-signal.

In accordance with still example another aspect of the present disclosure, a system for determining a suitable workout in consideration of a context includes at least one wearable device configured to measure a bio-signal of a user through reception of a request for bio-data from an electronic device and to transmit the measured bio-signal to the electronic device; the electronic device being configured to receive a command for executing a workout program, to request the bio-data from the at least one wearable device in order to collect context data for the user, to request surrounding environment data of the user from at least one service server, and to determine whether it is suitable for the user to perform planned workout content based on the collected context data; and the at least one service server being configured to search for surrounding environment information of the user through reception of the request for the surrounding environment data of the user from the electronic device and to transmit to the electronic device the surrounding environment data of the user according to the result of the search.

In accordance with still another example aspect of the present disclosure, a system for determining a suitable workout in consideration of a context includes an electronic device configured to receive a command for executing a workout program, to request surrounding environment data of a user from at least one service server in order to collect context data for the user, to measure a bio-signal of the user, and to determine whether it is suitable that the user performs planned workout content based on the collected context data and the measured bio-signal; and the at least one service server being configured to search for the surrounding environment information of the user through reception of the request for the surrounding environment data of the user from the electronic device and to transmit the surrounding environment data of the user according to the result of the search to the electronic device.

According to the various aspects of the present disclosure, it is possible to provide the electronic device, system, and method that can recommend the most suitable workout content to the user in consideration of the current context.

According to the various aspects of the present disclosure, it is possible to provide the electronic device, system, and method that can enable the user to perform more scientific workout and body (health) care in consideration of the various contexts.

BRIEF DESCRIPTION OF THE DRAWINGS

The above and/or other aspects, features and attendant advantages of the present disclosure will become apparent and more readily appreciated from the following detailed description, taken in conjunction with the accompanying drawings, in which like reference numerals refer to like elements, and wherein:

FIGS. 9, 10, 11, 12A, 12B, 13A, 13B and 14 are diagrams illustrating an example user interface according to various example embodiments of the present disclosure.

DETAILED DESCRIPTION

Figure 1:
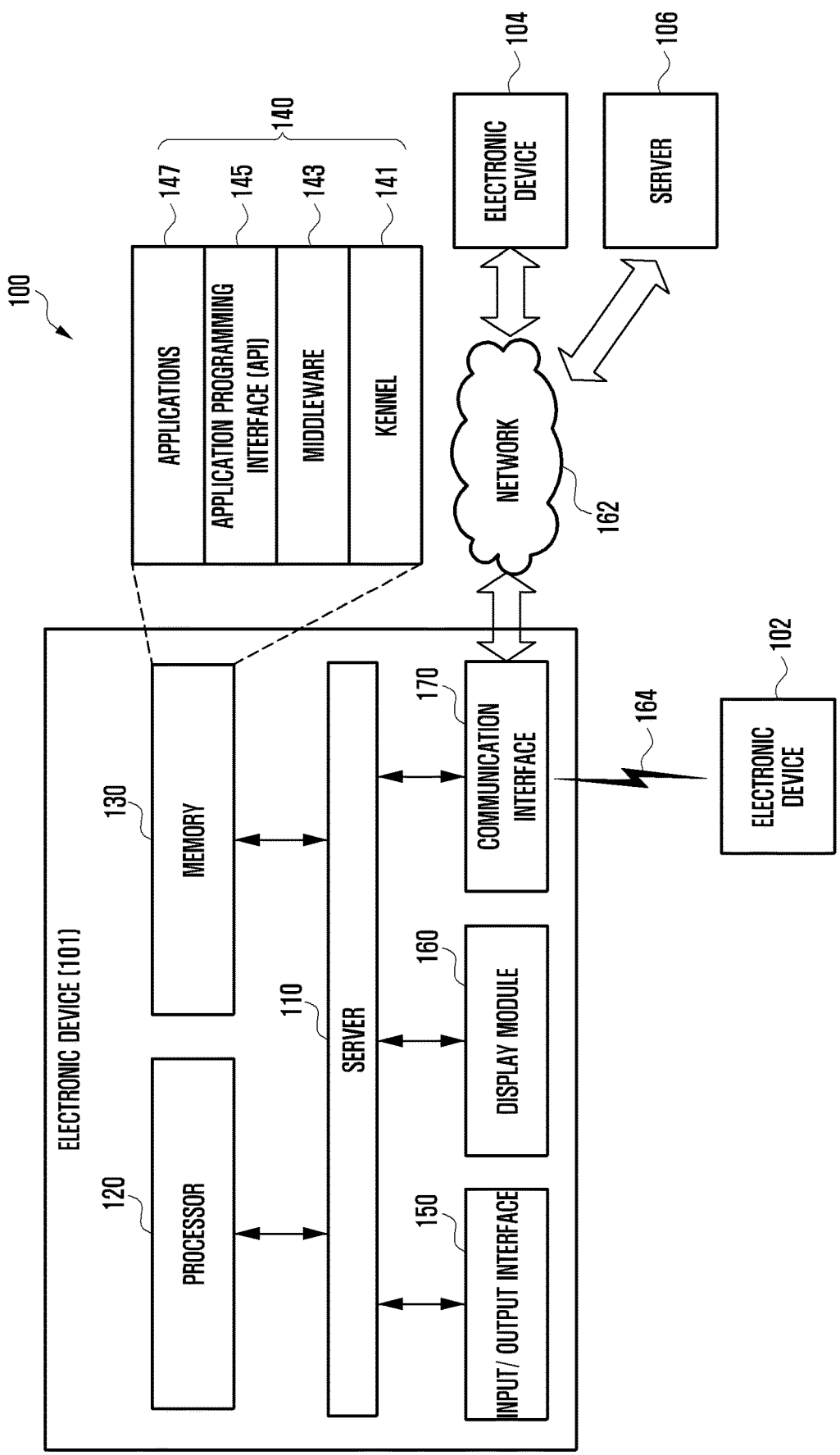
FIG. 1 is a diagram illustrating an example electronic device in a network environment according to various example embodiments of the present disclosure.

Hereinafter, various example embodiments of the present disclosure will be described with reference to the accompanying drawings. However, it should be understood that there is no intent to limit the present disclosure to the particular forms disclosed herein; rather, the present disclosure should be understood to cover various modifications, equivalents, and/or alternatives of embodiments of the present disclosure. In describing the drawings, similar reference numerals may be used to designate similar constituent elements.

As used herein, the expression "have", "may have", "include", or "may include" refers to the existence of a corresponding feature (e.g., numeral, function, operation, or constituent element such as component), and does not exclude one or more additional features.

In the present disclosure, the expression "A or B", "at least one of A or/and B", or "one or more of A or/and B" may include all possible combinations of the items listed. For example, the expression "A or B", "at least one of A and B", or "at least one of A or B" refers to all of (1) including at least one A, (2) including at least one B, or (3) including all of at least one A and at least one B.

The expression "a first", "a second", "the first", or "the second" used in various embodiments of the present disclosure may modify various components regardless of the order and/or the importance but does not limit the corresponding components. For example, a first user device and a second user device indicate different user devices although both of them are user devices. For example, a first element may be termed a second element, and similarly, a second element may be termed a first element without departing from the scope of the present disclosure.

It should be understood that when an element (e.g., first element) is referred to as being (operatively or communicatively) "connected," or "coupled," to another element (e.g., second element), it may be directly connected or coupled directly to the other element or any other element (e.g., third element) may be interposed between them. On the other hand, it may be understood that when an element (e.g., first element) is referred to as being "directly connected," or "directly coupled" to another element (second element), there are no element (e.g., third element) interposed between them.

The expression "configured to" used in the present disclosure may be used interchangeably with, for example, "suitable for", "having the capacity to", "designed to", "adapted to", "made to", or "capable of" according to the situation. The term "configured to" may not necessarily imply "specifically designed to" in hardware. Alternatively, in some situations, the expression "device configured to" may refer to a situation in which the device, together with other devices or components, "is able to". For example, the phrase "processor adapted (or configured) to perform A, B, and C" may refer to a dedicated processor (e.g. embedded processor) for performing the corresponding operations or a generic-purpose processor (e.g., central processing unit (CPU) or application processor (AP)) that can perform the corresponding operations by executing one or more software programs stored in a memory device.

The terms used in the present disclosure are only used to describe specific embodiments, and are not intended to limit the present disclosure. As used herein, singular forms may include plural forms as well unless the context clearly indicates otherwise. Unless defined otherwise, all terms used herein, including technical and scientific terms, have the same meaning as those commonly understood by a person skilled in the art to which the present disclosure pertains. Such terms as those defined in a generally used dictionary may be interpreted to have the meanings equal to the contextual meanings in the relevant field of art, and are not to be interpreted to have ideal or excessively formal meanings unless clearly defined in the present disclosure. In some cases, even if the term is defined in the present disclosure, it should not be interpreted to exclude embodiments of the present disclosure.

In this disclosure, an electronic device may be a device that involves a communication function. For example, an electronic device may be a smart phone, a tablet PC (Personal Computer), a mobile phone, a video phone, an e-book reader, a desktop PC, a laptop PC, a netbook computer, a PDA (Personal Digital Assistant), a PMP (Portable Multimedia Player), an MP3 player, a portable medical device, a digital camera, or a wearable device (e.g., an HMD (Head-Mounted Device) such as electronic glasses, electronic clothes, an electronic bracelet, an electronic necklace, an electronic accessory, an electronic tattoo, a smart mirror, or a smart watch), or the like, but is not limited thereto.

According to some embodiments, an electronic device may be a smart home appliance that involves a communication function. For example, an electronic device may be a TV, a DVD (Digital Video Disk) player, audio equipment, a refrigerator, an air conditioner, a vacuum cleaner, an oven, a microwave, a washing machine, an air cleaner, a set-top box, a TV box (e.g., Samsung HomeSync™, Apple TV™, Google TV™, etc.), a game console, an electronic dictionary, an electronic key, a camcorder, or an electronic picture frame, or the like, but is not limited thereto.

According to another embodiment, the electronic device may include at least one of various medical devices (e.g., various portable medical measuring devices (a blood glucose monitoring device, a heart rate monitoring device, a blood pressure measuring device, a body temperature measuring device, etc.), a Magnetic Resonance Angiography (MRA), a Magnetic Resonance Imaging (MRI), a Computed Tomography (CT) machine, and an ultrasonic machine), a navigation device, a Global Positioning System (GPS) receiver, an Event Data Recorder (EDR), a Flight Data Recorder (FDR), a Vehicle Infotainment Devices, an electronic devices for a ship (e.g., a navigation device for a ship, and a gyro-compass), avionics, security devices, an automotive head unit, a robot for home or industry, an automatic teller's machine (ATM) in banks, point of sales (POS) in a shop, or internet device of things (e.g., a light bulb, various sensors, electric or gas meter, a sprinkler device, a fire alarm, a thermostat, a streetlamp, a toaster, a sporting goods, a hot water tank, a heater, a boiler, etc.), or the like, but is not limited thereto.

According to some embodiments, an electronic device may be furniture or part of a building or construction having a communication function, an electronic board, an electronic signature receiving device, a projector, or various measuring instruments (e.g., a water meter, an electric meter, a gas meter, a wave meter, etc.), or the like, but is not limited thereto. An electronic device disclosed herein may be one of the above-mentioned devices or any combination thereof.

Hereinafter, an electronic device according to various embodiments will be described with reference to the accompanying drawings. As used herein, the term "user" may indicate a person who uses an electronic device or a device (e.g., an artificial intelligence electronic device) that uses an electronic device.

FIG. 1 is a diagram illustrating a network environment including an example electronic device according to various example embodiments of the present disclosure.

Referring to FIG. 1, an electronic device 101, in a network environment 100, includes a bus 110, a processor (e.g., including processing circuitry) 120, a memory 130, an input/output interface (e.g., including input/output circuitry) 150, a display 160, and a communication interface (e.g., including communication circuitry) 170. According to some embodiment, the electronic device 101 may omit at least one of the components or further include another component.

The bus 110 may be a circuit connecting the above described components and transmitting communication (e.g., a control message) between the above described components.

The processor 120 may include various processing circuitry, such as, for example, and without limitation, one or more of a dedicated processor, a central processing unit (CPU), an application processor (AP) or a communication processor (CP). For example, the processor 120 may control at least one component of the electronic device 101 and/or execute calculation relating to communication or data processing.

The memory 130 may include volatile and/or non-volatile memory. For example, the memory 130 may store command or data relating to at least one component of the electronic device 101. According to some embodiment, the memory may store software and/or program 140. For example, the program 140 may include a kernel 141, middleware 143, an application programming interface (API) 145, and/or an application 147 and so on. At least one portion of the kernel 141, the middleware 143 and the API 145 may be defined as operating system (OS).

The kernel 141 controls or manages system resources (e.g., the bus 110, the processor 120, or the memory 130) used for executing an operation or function implemented by the remaining other program, for example, the middleware 143, the API 145, or the application 147. Further, the kernel 141 provides an interface for accessing individual components of the electronic device 101 from the middleware 143, the API 145, or the application 147 to control or manage the components.

The middleware 143 performs a relay function of allowing the API 145 or the application 147 to communicate with the kernel 141 to exchange data. Further, in operation requests received from the application 147, the middleware 143 performs a control for the operation requests (e.g., scheduling or load balancing) by using a method of assigning a priority, by which system resources (e.g., the bus 110, the processor 120, the memory 130 and the like) of the electronic device 101 may be used, to the application 147.

The API 145 is an interface by which the application 147 may control a function provided by the kernel 141 or the middleware 142 and includes, for example, at least one interface or function (e.g., command) for a file control, a window control, image processing, or a character control.

The input/output interface 150 may include various input/output circuitry and be an interface to transmit command or data inputted by a user or another external device to another component(s) of the electronic device 101. Further, the input/output interface 150 may output the command or data received from the another component(s) of the electronic device 101 to the user or the another external device.

The display 160 may include, for example, liquid crystal display (LCD), light emitting diode (LED), organic LED (OLED), or micro electro mechanical system (MEMS) display, or electronic paper display, or the like, but is not limited thereto. The display 160 may display, for example, various contents (text, image, video, icon, or symbol, and so on) to a user. The display 160 may include a touch screen, and receive touch, gesture, approaching, or hovering input using a part of body of the user.

The communication interface 170 may include various communication circuitry and set communication of the electronic device 101 and external device (e.g., a first external device 102, a second external device 104, or a server 106). For example, the communication interface 170 may be connected with the network 162 through wireless communication or wire communication and communicate with the external device (e.g., a second external device 104 or server 106). Additionally, the communication interface 170 may be connected with the first electronic device 102 over a short-range wireless communication connection 164.

Wireless communication may use, as cellular communication protocol, at least one of LTE (long-term evolution), LTE-A (LTE Advance), CDMA (code division multiple access), WCDMA (wideband CDMA), UMTS (universal mobile telecommunications system), WiBro (Wireless Broadband), GSM (Global System for Mobile Communications), and the like, for example. A short-range communication 164 may include, for example, at least one of Wi-Fi, Bluetooth, Near Field Communication (NFC), and Global Navigation Satellite System (GNSS), and the like.

The GNSS may include at least one of, for example, a Global Positioning System (GPS), a Global navigation satellite system (Glonass), a Beidou Navigation Satellite System (hereinafter, referred to as "Beidou"), and Galileo (European global satellite-based navigation system). Hereinafter, the "GPS" may be interchangeably used with the "GNSS" in the present disclosure. Wired communication may include, for example, at least one of USB (universal serial bus), HDMI (high definition multimedia interface), RS-232 (recommended standard-232), POTS (plain old telephone service), and the like. The network 162 may include telecommunication network, for example, at least one of a computer network (e.g., LAN or WAN), internet, and a telephone network.

Each of the first external device 102 and the second external device 104 may be same type or different type of device with the electronic device 101. According to some embodiment, the server 106 may include one or more group of servers. According to various embodiments, at least one portion of executions executed by the electronic device may be performed by one or more electronic devices (e.g., external electronic device 102, 104, or server 106). According to some embodiments, when the electronic device 101 should perform a function or service automatically, the electronic device 101 may request performing of at least one function to the another device (e.g., external electronic device 102, 104, or server 106). For the above, cloud computing technology, distributed computing technology, or client-server computing technology may be used, for example.

Figure 2:
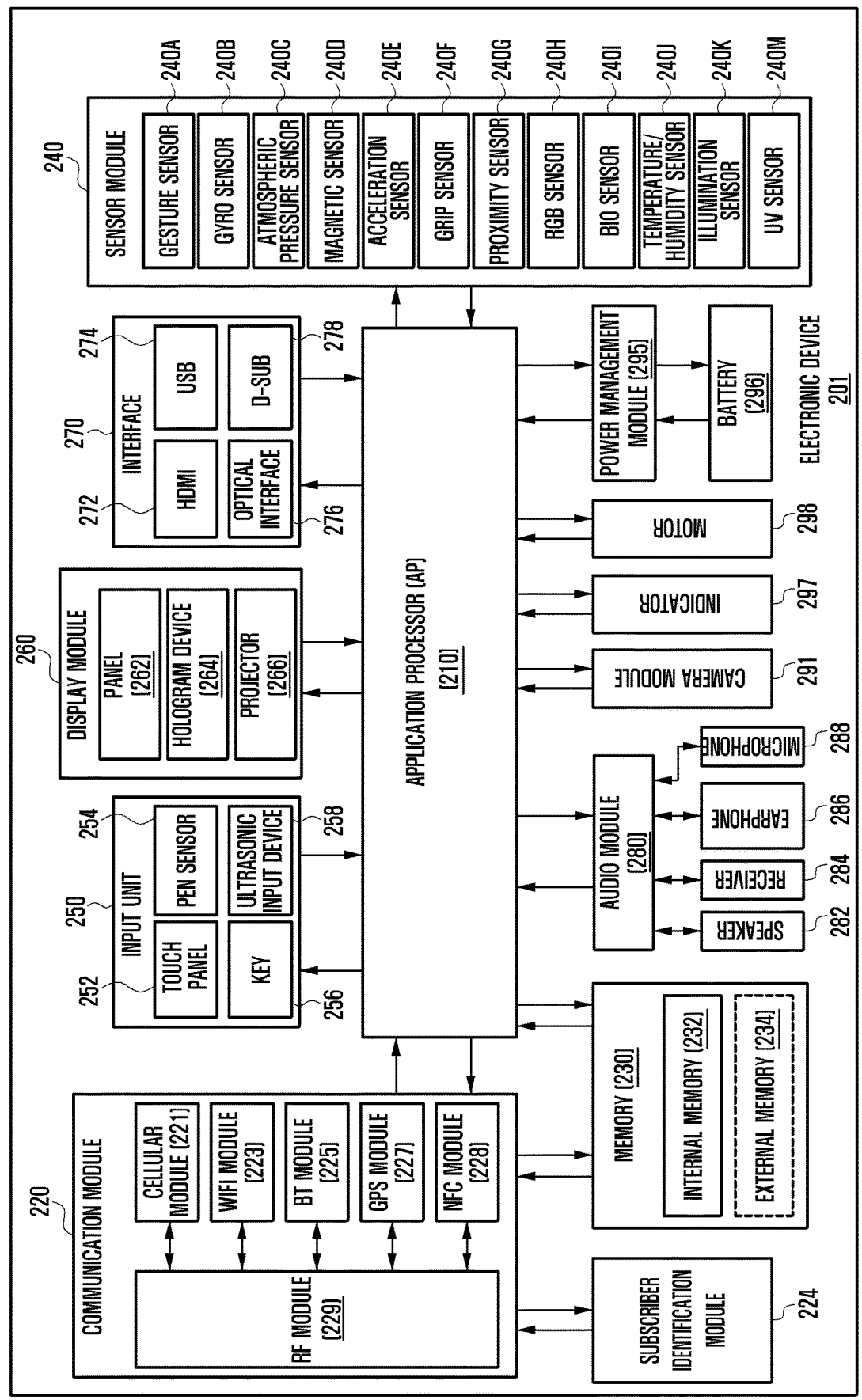
FIG. 2 is a block diagram illustrating an example configuration of an electronic device according to various example embodiments of the present disclosure.

FIG. 2 is a block diagram illustrating an example electronic device according to an example embodiment of the present disclosure.

Referring to FIG. 2, an electronic device 201 may include, for example, a whole or a part of the electronic device 101 illustrated in FIG. 1. The electronic device 201 includes one or more APs (e.g., including processing circuitry) 210, a communication module (e.g., including communication circuitry) 220, a subscriber identification module (SIM) card 224, a memory 230, a sensor module 240, an input device (e.g., including input circuitry) 250, a display 260, an interface (e.g., including interface circuitry) 270, an audio module 280, a camera module 291, a power managing module 295, a battery 296, an indicator 297, and a motor 298.

The AP 210 may include various processing circuitry and operates an OS or an application program so as to control a plurality of hardware or software component elements connected to the AP 210 and execute various data processing and calculations including multimedia data. The AP 210 may be implemented by, for example, a system on chip (SoC). According to an embodiment, the processor 210 may further include a graphics processing unit (GPU) and/or image signal processor. The AP 210 may include at least one portion of components illustrated in FIG. 2 (e.g., a cellular module 221). The AP 210 may load command or data received from at least one of another component (e.g., non-volatile memory), store various data in the non-volatile memory.

The communication module 220 may include same or similar components with the communication interface 170 of FIG. 1. The communication module 220, for example, may include various communication circuitry, including without limitation, the cellular module 221, a Wi-Fi module 223, a BT module 225, a GPS module 227, a NFC module 228, and a radio frequency (RF) module 229.

The cellular module 221 provides a voice, a call, a video call, a short message service (SMS), or an internet service through a communication network (e.g., LTE, LTE-A, CDMA, WCDMA, UMTS, WiBro, GSM and the like). Further, the cellular module 221 may distinguish and authenticate electronic devices within a communication network by using a SIM (e.g., the SIM card 224). According to an embodiment, the cellular module 221 performs at least some of the functions which may be provided by the AP 210. For example, the cellular module 221 may perform at least some of the multimedia control functions. According to an embodiment, the cellular module 221 may include a CP.

Each of the Wi-Fi module 223, the BT module 225, the GPS module 227, and the NFC module 228 may include, for example, a processor for processing data transmitted/received through the corresponding module. Although the cellular module 221, the Wi-Fi module 223, the BT module 225, the GPS module 227, and the NFC module 228 are at least some (e.g., two or more) of the cellular module 221, the Wi-Fi module 223, the BT module 225, the GPS module 227, and the NFC module 228 may be included in one integrated chip (IC) or one IC package according to one embodiment. For example, at least some (e.g., the CP corresponding to the cellular module 221 and the Wi-Fi processor corresponding to the Wi-Fi module 222 of the processors corresponding to the cellular module 221, the Wi-Fi module 223, the BT module 225, the GPS module 227, and the NFC module 228 may be implemented by one SoC.

The RF module 229 transmits/receives data, for example, an RF signal. Although not illustrated, the RF module 229 may include, for example, a transceiver, a power amp module (PAM), a frequency filter, a low noise amplifier (LNA) and the like. Further, the RF module 229 may further include a component for transmitting/receiving electronic waves over a free air space in wireless communication, for example, a conductor, a conducting wire, and the like. Although the cellular module 221, the Wi-Fi module 223, the BT module 225, the GPS module 227, and the NFC module 228 share one RF module 229 in FIG. 2, at least one of the cellular module 221, the Wi-Fi module 223, the BT module 225, the GPS module 227, and the NFC module 228 may transmit/receive an RF signal through a separate RF module according to one embodiment.

The SIM card 224 is a card including a SIM and may be inserted into a slot formed in a particular portion of the electronic device. The SIM card 224 includes unique identification information (e.g., integrated circuit card identifier (ICCID)) or subscriber information (e.g., international mobile subscriber identity (I MSI).

The memory 230 (e.g., memory 130) may include an internal memory 232 and/or an external memory 234. The internal memory 232 may include, for example, at least one of a volatile memory (e.g., a random access memory (RAM), a dynamic RAM (DRAM), a static RAM (SRAM), a synchronous dynamic RAM (SDRAM), and the like), and a non-volatile Memory (e.g., a read only memory (ROM), a one time programmable ROM (OTPROM), a programmable ROM (PROM), an erasable and programmable ROM (EPROM), an electrically erasable and programmable ROM (EEPROM), a mask ROM, a flash ROM, a not and (NAND) flash memory, a not or (NOR) flash memory, and the like).

According to an embodiment, the internal memory 232 may be a solid state drive (SSD). The external memory 234 may further include a flash drive, for example, a compact flash (CF), a secure digital (SD), a micro-SD, a mini-SD, an extreme digital (xD), or a memory stick. The external memory 234 may be functionally connected to the electronic device 201 through various interfaces. According to an embodiment, the electronic device 201 may further include a storage device (or storage medium) such as a hard drive.

The sensor module 240 measures a physical quantity or detects an operation state of the electronic device 201, and converts the measured or detected information to an electrical signal. The sensor module 240 may include, for example, at least one of a gesture sensor 240A, a gyro sensor 240B, an atmospheric pressure (barometric) sensor 240C, a magnetic sensor 240D, an acceleration sensor 240E, a grip sensor 240F, a proximity sensor 240G, a color sensor 240H (e.g., red, green, and blue (RGB) sensor) 240H, a biometric (e.g., bio) sensor 240I, a temperature/humidity sensor 240J, an illumination (e.g., light) sensor 240K, and a ultraviolet (UV) sensor 240M. Additionally or alternatively, the sensor module 240 may include, for example, an E-nose sensor, an electromyography (EMG) sensor, an electroencephalogram (EEG) sensor, an electrocardiogram (ECG) sensor, an photoplethysmogram (PPG) sensor, an infrared (IR) sensor, an iris sensor, a fingerprint sensor (not illustrated), and the like. The sensor module 240 may further include a control circuit for controlling one or more sensors included in the sensor module 240.

The input device 250 may include various input circuitry, such as, for example, and without limitation, a touch panel 252, a (digital) pen sensor 254, a key 256, and an ultrasonic input device 258. For example, the touch panel 252 may recognize a touch input in at least one type of a capacitive type, a resistive type, an infrared type, and an acoustic wave type. The touch panel 252 may further include a control circuit. In the capacitive type, the touch panel 252 may recognize proximity as well as a direct touch. The touch panel 252 may further include a tactile layer. In this event, the touch panel 252 provides a tactile reaction to the user.

The (digital) pen sensor 254 may be implemented, for example, using a method identical or similar to a method of receiving a touch input of the user, or using a separate recognition sheet. The key 256 may include, for example, a physical button, an optical key, or a key pad. The ultrasonic input device 258 is a device which may detect an acoustic wave by a microphone (e.g., a microphone 288) of the electronic device 201 through an input means generating an ultrasonic signal to identify data and may perform wireless recognition. According to an embodiment, the electronic device 201 receives a user input from an external device (e.g., computer or server) connected to the electronic device 201 by using the communication module 220.

The display 260 (e.g., display 160) includes a panel 262, a hologram device 264, and a projector 266. The panel 262 may be, for example, a LCD or an active matrix OLED (AM-OLED). The panel 262 may be implemented to be, for example, flexible, transparent, or wearable. The panel 262 may be configured by the touch panel 252 and one module. The hologram device 264 shows a stereoscopic image in the air by using interference of light. The projector 266 projects light on a screen to display an image. For example, the screen may be located inside or outside the electronic device 201. According to an embodiment, the display 260 may further include a control circuit for controlling the panel 262, the hologram device 264, and the projector 266.

The interface 270 may include various interface circuitry, such as, for example, and without limitation, an HDMI 272, a USB 274, an optical interface 276, and a D-subminiature (D-sub) 278. The interface 270 may be included in, for example, the communication interface 170 illustrated in FIG. 1. Additionally or alternatively, the interface 270 may include, for example, a mobile high-definition link (MHL) interface, an SD card/multi-media card (MMC), or an infrared data association (IrDA) standard interface.

The audio module 280 bi-directionally converts a sound and an electronic signal. At least some components of the audio module 280 may be included in, for example, the input/output interface 150 illustrated in FIG. 1. The audio module 280 processes sound information input or output through, for example, a speaker 282, a receiver 284, an earphone 286, the microphone 288 and the like.

The camera module 291 is a device which may photograph a still image and a video. According to an embodiment, the camera module 291 may include one or more image sensors (e.g., a front sensor or a back sensor), an image signal processor (ISP) (not shown) or a flash (e.g., an LED or xenon lamp).

The power managing module 295 manages power of the electronic device 201. Although not illustrated, the power managing module 295 may include, for example, a power management integrated circuit (PMIC), a charger IC, or a battery or fuel gauge.

The PMIC may be mounted to, for example, an integrated circuit or a SoC semiconductor. A charging method may be divided into wired and wireless methods. The charger IC charges a battery and prevent over voltage or over current from flowing from a charger. According to an embodiment, the charger IC includes a charger IC for at least one of the wired charging method and the wireless charging method. The wireless charging method may include, for example, a magnetic resonance method, a magnetic induction method and an electromagnetic wave method, and additional circuits for wireless charging, for example, circuits such as a coil loop, a resonant circuit, a rectifier and the like may be added.

The battery fuel gauge measures, for example, a remaining quantity of the battery 296, or a voltage, a current, or a temperature during charging. The battery 296 may store or generate electricity and supply power to the electronic device 201 by using the stored or generated electricity. The battery 296 may include a rechargeable battery or a solar battery.

The indicator 297 shows particular statuses of the electronic device 201 or a part (e.g., AP 210) of the electronic device 201, for example, a booting status, a message status, a charging status and the like. The motor 298 converts an electrical signal to a mechanical vibration. Although not illustrated, the electronic device 201 may include a processing unit (e.g., GPU) for supporting a module TV. The processing unit for supporting the mobile TV may process, for example, media data according to a standard of digital multimedia broadcasting (DMB), digital video broadcasting (DVB), media flow and the like.

Each of the components of the electronic device according to various embodiments of the present disclosure may be implemented by one or more components and the name of the corresponding component may vary depending on a type of the electronic device. The electronic device according to various embodiments of the present disclosure may include at least one of the above described components, a few of the components may be omitted, or additional components may be further included. Also, some of the components of the electronic device according to various embodiments of the present disclosure may be combined to form a single entity, and thus may equivalently execute functions of the corresponding components before being combined.

Figure 3:
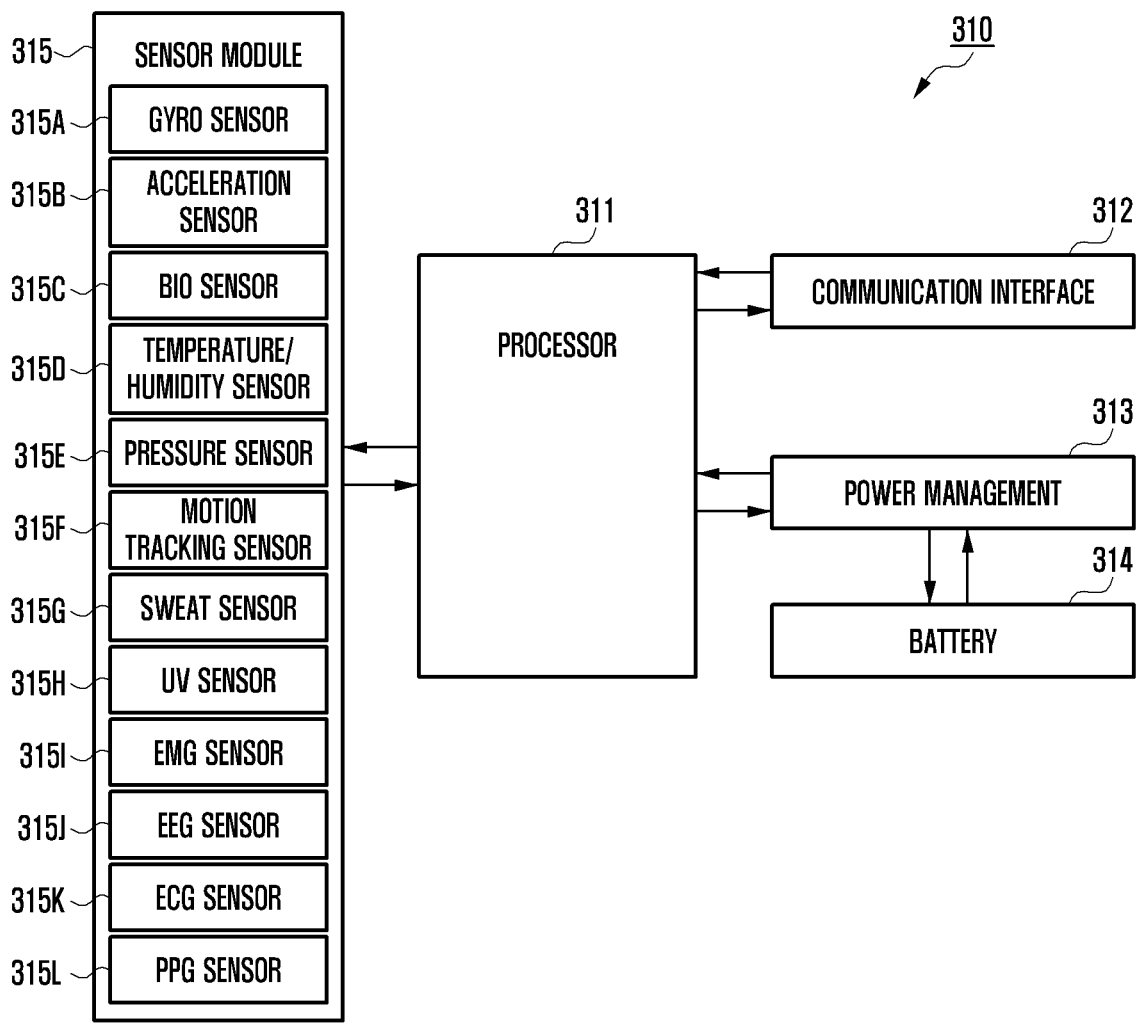
FIG. 3 is a block diagram illustrating an example configuration of a wearable device according to various example embodiments of the present disclosure.

FIG. 3 is a block diagram illustrating an example configuration of an example wearable device according to various example embodiments of the present disclosure;

The wearable device 310 includes one or more processor (e.g., including processing circuitry) 311, a communication interface (e.g., including communication circuitry) 312, a power managing module 313, a battery 314, and a sensor module 315.

The processor 311 may include various processing circuitry, such as, for example, and without limitation, one or more of a dedicated processor, a central processing unit (CPU), an application processor (AP) or a communication processor (CP). For example, the processor 311 may control at least one component of the wearable device 310 and/or execute calculation relating to communication or data processing.

The communication interface 312 may include various communication circuitry and be connected with the network 162 through wireless communication or wired communication and communicate with the external device.

Wireless communication may use, as cellular communication protocol, at least one of LTE (long-term evolution), LTE-A (LTE Advance), CDMA (code division multiple access), WCDMA (wideband CDMA), UMTS (universal mobile telecommunications system), WiBro (Wireless Broadband), GSM (Global System for Mobile Communications), and the like, for example. Wireless communication may include, for example, at least one of Wi-Fi, Bluetooth, BLE, Zigbee, Near Field Communication (NFC), Magnetic Secure Transmission, Radio Frequency (RF), Body Area Network (BAN) and Global Navigation Satellite System (GNSS), and the like.

The GNSS may include at least one of, for example, a Global Positioning System (GPS), a Global navigation satellite system (Glonass), a Beidou Navigation Satellite System (hereinafter, referred to as "Beidou"), and Galileo (European global satellite-based navigation system). Hereinafter, the "GPS" may be interchangeably used with the "GNSS" in the present disclosure. Wired communication may include, for example, at least one of USB (universal serial bus), HDMI (high definition multimedia interface), RS-232 (recommended standard-232), POTS (plain old telephone service), and the like. The network 162 may include telecommunication network, for example, at least one of a computer network (e.g., LAN or WAN), internet, and a telephone network.

The power managing module 313 manages power of the wearable device 310. Although not illustrated, the power managing module 313 may include, for example, a power management integrated circuit (PMIC), a charger IC, or a battery or fuel gauge.

The PMIC may be mounted to, for example, an integrated circuit or a SoC semiconductor. A charging method may be divided into wired and wireless methods. The charger IC charges a battery and prevent over voltage or over current from flowing from a charger. According to an embodiment, the charger IC includes a charger IC for at least one of the wired charging method and the wireless charging method. The wireless charging method may include, for example, a magnetic resonance method, a magnetic induction method and an electromagnetic wave method, and additional circuits for wireless charging, for example, circuits such as a coil loop, a resonant circuit, a rectifier and the like may be added.

The sensor module 315 may include various sensors and measures a physical quantity or detects an operation state of the wearable device 310, and converts the measured or detected information to an electrical signal. The sensor module 315 may include, for example, at least one of a gyro sensor 315A, an acceleration sensor 315B, a biometric (e.g., bio) sensor 315C, a temperature/humidity sensor 315D, pressure sensor 315E, a motion tracking sensor 315F, a sweat sensor 315G, a ultraviolet (UV) sensor 315H, an electromyography (EMG) sensor 315I, an electroencephalogram (EEG) sensor 315J, an electrocardiogram (ECG) sensor 315K, and an photoplethysmogram (PPG) sensor 315L. The sensor module 315 may further include a control circuit for controlling one or more sensors included in the sensor module 315.

According to various embodiments of the present disclosure, various elements of a wearable device 310 may be configured to be detachable because the wearable device 310 may be in the form of clothes; thus, its elements that are electrically connected to each other may be damaged during washing thereof. In an example embodiment, the wearable device 310 may be processed with waterproof coating to prevent the elements from being damaged by exposure to moisture.

Figure 4A:
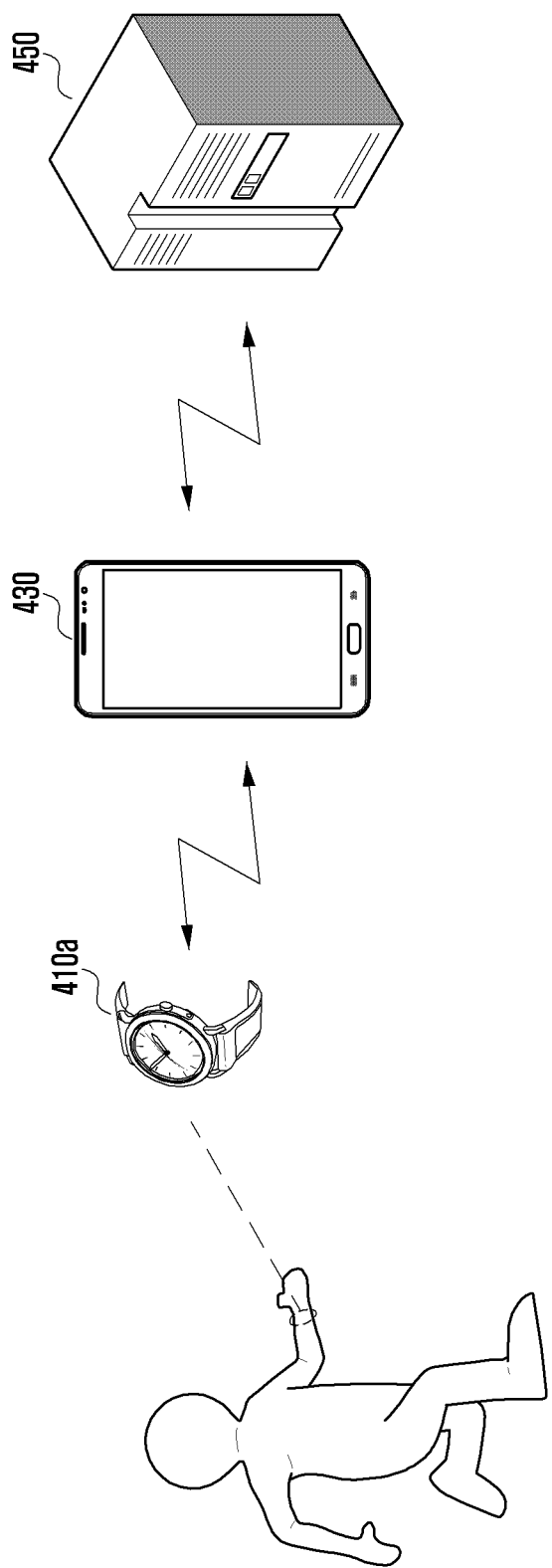
FIGS. 4A and 4B are diagrams illustrating an example environment of a system for determining a suitable workout in consideration of a context according to various example embodiments of the present disclosure.
Figure 4B:
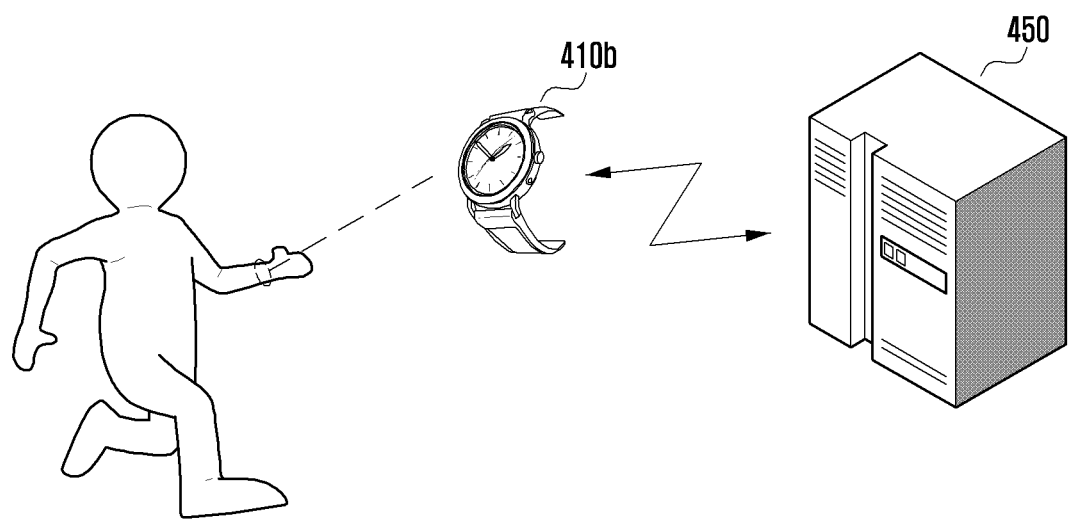

FIGS. 4A and 4B are diagrams illustrating an environment of an example system for determining a suitable workout in consideration of a context according to various example embodiments of the present disclosure.

Referring to FIG. 4A, a first system according to the present disclosure may include a wearable device 410a, an electronic device 430, and a service server 450. Further, referring to FIG. 4B, a second system according to the present disclosure may include a wearable device 410b and a service server 450.

In the first system as illustrated in FIG. 4A, the wearable device 410a may communicate with other external electronic devices through at least one other electronic device 430. On the other hand, in the second system as illustrated in FIG. 4B, the wearable device 410b may directly communicate with other external electronic devices.

In the description, the wearable device is used to include both the wearable device 410a and the wearable device 410b, and it is not used to be limited to any one specific system.

According to various embodiments, the wearable device 410a or 410b may measure a bio-signal of a user who wears the wearable device 410a or 410b. The wearable device 410a or 410b may include at least one of an accessory type (e.g., watch, ring, bracelet, anklet, necklace, glasses, contact lens, or Head-Mounted Device (HMD)), a fabric or garment-integrated type (e.g., e-clothing), a body-mounted type (e.g., skin pad or tattoo), and a bio-implantable circuit, or the like, but is not limited thereto. If the wearable device 410a or 410b is of the fabric or garment-integrated type, it may be in the form of at least one of T-shirt, trousers, and underwear, or the like, but is not limited thereto. In an example embodiment, the wearable device 410a or 410b may be in the form of at least one of socks, gloves, shoes, belt, and trousers, or the like, but is not limited thereto.

Bio-signals that are measured by such a wearable device 410a or 410b may refer to, for example, signals of heartbeat, Electrocardiogram (ECG), Photoplethysmogram (PPG), breath, body fat, acceleration, body size, or Electromyogram (EMG). The wearable device 410a or 410b may include a sensor module, and such a sensor module may be an Electrocardiogram (ECG) sensor, a Photoplethysmography (PPG) sensor, an acceleration sensor, an Electromyogram (EMG) sensor, a breath sensor, or a body fat sensor. Further, in a certain embodiment, the wearable device 410a or 410b may omit at least one sensor module or may be additionally provided with other elements.

According to various embodiments, if it is necessary for the electronic device 420 to measure user's bio-data, the electronic device 420 may request the wearable device 410a to provide at least a partial function related to a function or a service of the electronic device 420 instead of or in addition to self-execution of the function or the service. For example, the wearable device 410a may measure the bio-signal using the sensor module, and it may transmit the measured bio-signal to the electronic device 420 through a communication interface.

Although not illustrated, two or more wearable devices may be used in one system. In the case where a plurality of wearable devices transmit user's bio-signals, they may be configured to periodically transmit the user's bio-signals so as to prevent the occurrence of signal overlapping.

Figure 5:
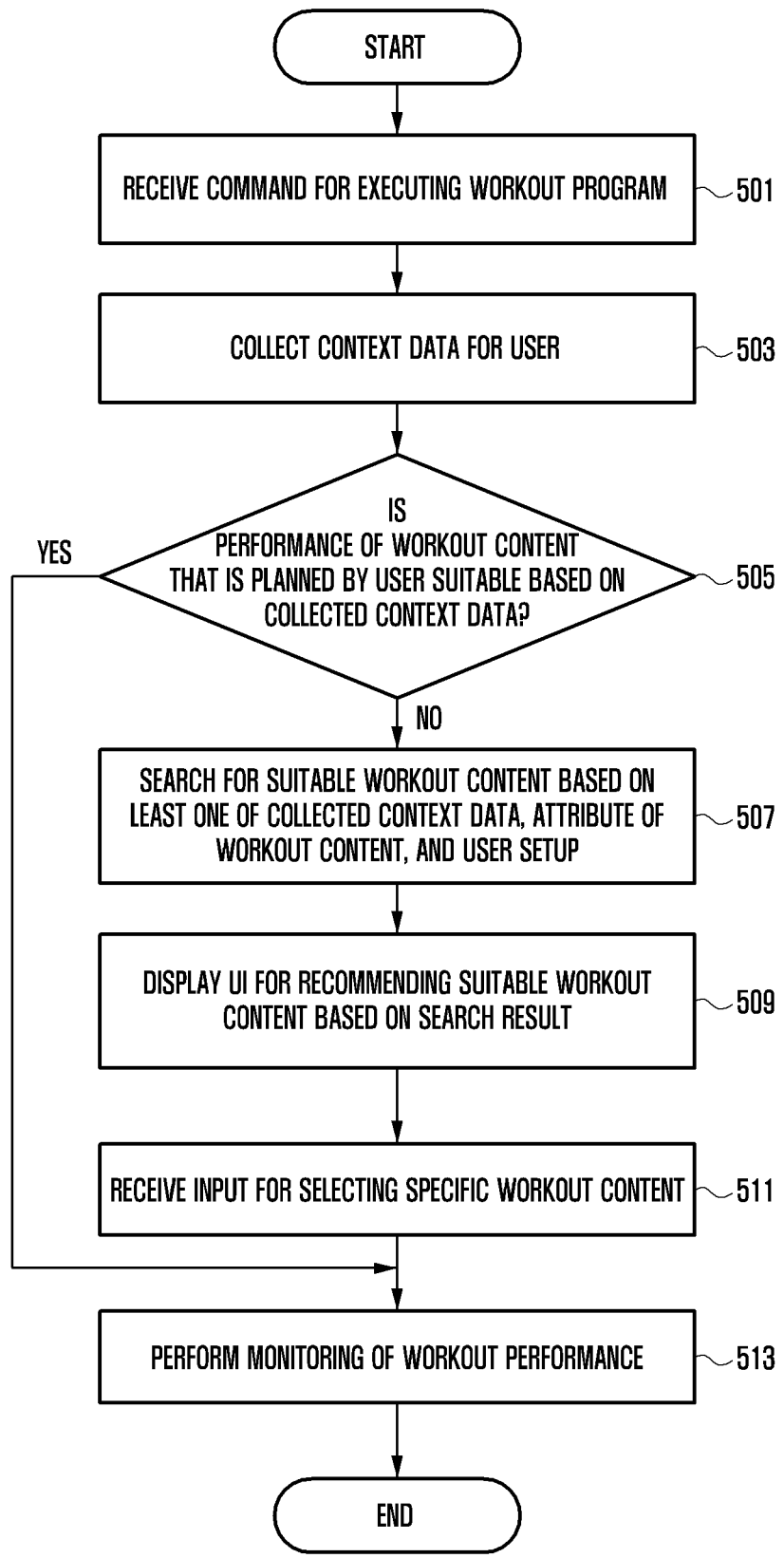
FIG. 5 is a flowchart illustrating an example method of an electronic device (or a wearable device) for determining a suitable workout in consideration of a context according to various example embodiments of the present disclosure.

FIG. 5 is a flowchart illustrating an example method of an electronic device (or a wearable device) for determining a suitable workout in consideration of a context according to various example embodiments of the present disclosure.

Referring to FIG. 5, at operation 501, an electronic device or a wearable device (hereinafter referred to as "electronic device") may receive a command for executing a workout program. The command may be received from a user or another electronic device (e.g., external electronic device or server). Further, in a certain embodiment, if a preset context occurs, it may be set to execute a workout program. The preset context may be, for example, a case where a specific time arrives, a case where it is recognized that a user is located in a specific place, or a case where a preset period arrives. In addition, it is also possible to set a workout program to be executed in various specific contexts.

At operation 503, the electronic device may collect context data for the user. The context data may mean data that includes all contexts that are considered to determine a suitable workout. For example, the context data may include all pieces of information that are required to determine suitable workout content, such as personal information of the user, surrounding environment information of the user, and reference information.

According to various embodiments, the context data may be acquired from the user, a sensor included in the electronic device, and other external electronic devices through various reception paths.

Figure 6:
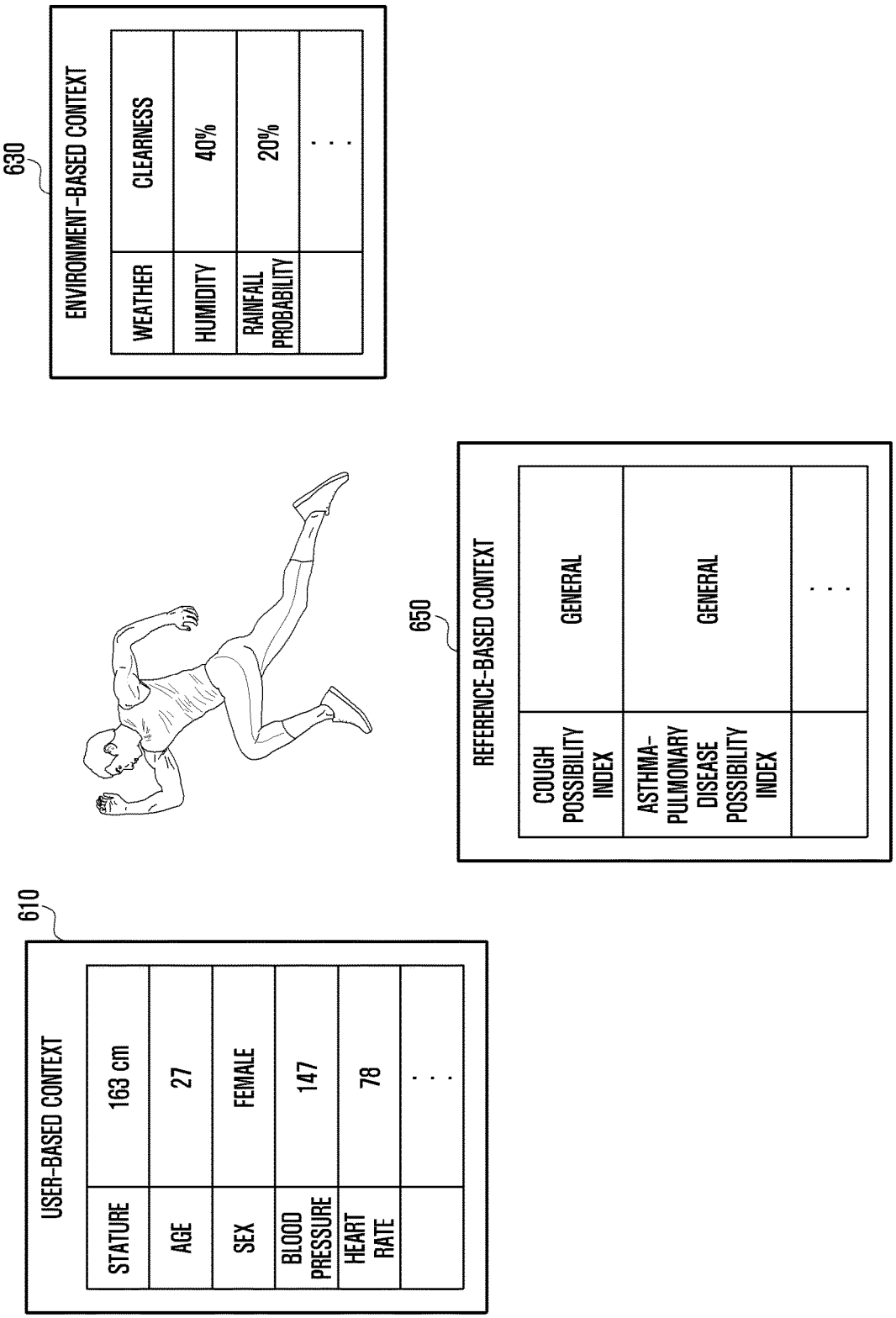
FIG. 6 is a diagram illustrating an example concept of context data according to various example embodiments of the present disclosure.

FIG. 6 is a diagram illustrating an example concept of context data according to various example embodiments of the present disclosure.

According to various embodiments, the context data may include user-based context data 610, environment-based context data 630, and reference-based context data 650.

The user-based context data 610 may include bio-data and personal record data. The bio-data may refer, for example, to a user's current bio-information that is acquired in real time through sensors, such as the number of steps, blood pressure, heart rate, stress index, and blood oxygen saturation. On the other hand, the personal record data may refer, for example, to user's inherent bio-information that is pre-stored in a memory. For example, the personal record data may include body information that is acquired on the basis of a user input, such as a user's stature, age, sex, presence or absence of disease, and menstrual cycle; accumulated personal record information, such as sleep time on the day, calorie consumption on the day, workout time on the day, and accumulated workout time; and analysis information that is acquired on the basis of the personal record data, such as average calorie intake, average calorie consumption, average workout time, average sleep time, average stress index, average heart rate, maximum heart rate, heart rate at rest, basal metabolic rate, average blood pressure, and average blood sugar level.

The environment-based context data 630 may refer, for example, to information indicating at least a surrounding environment of a user, such as surrounding weather of a user, humidity, fine dust concentration, an atmospheric temperature, a wind direction, a wind speed, an altitude, an ultraviolet ray index, a rainfall probability, a rainfall amount, and a wave height. In the description, although it is stated that the environment-based context data is acquired through a service server 450 of the electronic device, it may be directly acquired through sensors included in the electronic device.

The reference-based context data 650 may refer, for example, to information that is acquired with reference to references, such as a cough possibility index, an asthma-pulmonary disease possibility index, a stroke possibility index, and a skin disease possibility index.

At operation 505, the electronic device may determine whether it is suitable for the user to perform a planned workout content based on the collected context data.

According to various embodiments, the electronic device may pre-store the workout content that is planned to be performed by the user; and, in a certain embodiment, the electronic device may receive the workout content from another external electronic device. Further, the workout content may be manually planned by the user, or it may be planned by the electronic device or the other external electronic device using an algorithm in accordance with a target value that is designated by the user. For example, if the user inputs the target value, the algorithm may distribute a proper plan that can achieve the target value.

According to various embodiments, the electronic device may determine whether the workout performance is suitable in consideration of a place in which the workout is performed, a user's workout purpose, or a user's workout style. For example, if it is planned that the user performs an outdoor workout and the collected context data indicates that the outdoor workout is unsuitable (e.g., 90% rainfall probability, very bad fine dust concentration, high ultraviolet index, or high asthma-pulmonary disease possibility index), the electronic device may determine that it is unsuitable for the workout content planned by the user to be performed. Further, in a certain embodiment, if a user who aims at rehabilitation therapy plans a workout content that may disturb the user's rehabilitation therapy, the electronic device may determine that it is unsuitable for the workout content planned by the user to be performed. Further, in a certain embodiment, if a user plans a specific workout content that has a very low target attainment rate, the electronic device may determine that it imposes too much burden on the user and that it is unsuitable to enforce the performance of the specific workout content.

At operation 505, if the electronic device determines that performance of the planned workout content is unsuitable, the process may move to operation 507. At operation 507, the electronic device may search for suitable workout content based on at least one of collected context data, attribute of the workout content, and user setup.

In order to recommend suitable workout content, the electronic device may consider a user's preference for the workout content among the collected context data. The user's preference for the workout content may be manually input by the user, or it may be automatically determined by the electronic device in consideration of the target attainment rate and performance frequency.

The attribute of the workout content may mean, for example, the self-attribute of the workout content, such as a workout content performance place (e.g., indoor workout or outdoor workout), a performance time, the degree of movement, and operation difficulty.

The user setup may mean a user's workout purpose (e.g., diet, physical strength enhancement, or health maintenance) and a user's workout style (e.g., kind and strength of a preferential workout).

According to various embodiments, in order to recommend suitable workout content, the electronic device may store workout content that is suitable for the collected context data, attributes of the workout content, and user setup in the form of a table. For example, Table 1 shows an example of storing the workout content that is suitable for the collected context data, attributes of the workout content, and user setup in the form of a table.

TABLE 1

| Workout content | Suitable environment | Performance place | Workout purpose | User preference | Strength |
|---|---|---|---|---|---|
| Running | Fine | Outdoor | Diet | Middle | Middle |
| Treadmill | — | Indoor | Diet | High | Middle |
| Skiing | Low temperature | Outdoor | Physical training | Low | Middle |
| Walking | Fine | Outdoor | Health care | High | Low |
| Yoga | — | Indoor | Diet | High | Middle |
| Aerobic | — | Indoor | Diet | High | High |
| Plank | — | Indoor | Diet | Middle | High |
| Squat | — | Indoor | Diet | High | High |
| Lunge | — | Indoor | Physical training | Middle | High |
| Step-up | — | Indoor | Physical training | Low | Middle |
| Mountain climbing | Fine | Outdoor | Physical training | Low | High |

Referring to Table 1, for example, it is assumed that the user's workout purpose is diet, and workouts having middle or low strength are suitable. On a day with heavy rainfall, the electronic device may search for treadmill or yoga as suitable workout content with reference to Table 1. Further, in a certain embodiment, it is assumed that the user's workout purpose is physical training, and workouts having high strength are suitable. If it is determined that the user desires an outdoor workout on a fine day, the electronic device may search for mountain climbing as suitable workout content. Table 1 merely exemplifies the storing of various pieces of workout content and their attributes in the form of a table, and because it is apparent to those of ordinary skill in the art that workout content and attributes can be further added or omitted, a detailed explanation thereof will be omitted.

At operation 509, the electronic device may display a UI for recommending suitable workout content based on the search result. For example, if the search reveals that suitable workout content is treadmill or yoga, the electronic device may control the display to display a UI for recommending treadmill or yoga. Further, in a certain embodiment, if the search reveals that the suitable workout content is mountain climbing, the electronic device may control the display to display a UI for recommending mountain climbing.

Further, the UI for recommending suitable workout content may be configured to display previously planned workout content together. Even if it is determined that the performance of the previously planned workout content is unsuitable as a result of the determination by the electronic device, a determination on whether to perform the workout content may be made through a user's selection.

Operation 509 is not an essential element of the present disclosure and thus may be omitted. In this case, the electronic device may select workout content that is determined most suitable, and thus operation 511 may also be omitted.

At operation 511, the electronic device may receive an input for selecting specific workout content based on the UI for recommending the suitable workout content.

According to various embodiments, the specific workout content may be selected through a user's manual input, or it may be automatically selected in accordance with a pre-stored algorithm. The pre-stored algorithm may be, for example, an algorithm which pre-stores specific context if an input for selecting the specific workout content is not received for a preset period or if it is determined that the user is performing the specific workout content, and it enables the electronic device to automatically select the specific workout content to match the specific context if the stored specific context occurs.

At operation 513, the electronic device may monitor the user's workout performance. For example, if it is determined at operation 505 that it is suitable for the planned workout content to be performed, the electronic device may monitor bio-data and motion tracking data of the user who performs the planned workout content. Further, in a certain embodiment, the electronic device may monitor the bio-data and the motion tracking data of the user who performs the specific workout content that is selected at operation 511. The bio-data and the motion tracking data as monitored above may be collected and stored, and the user-based context data may be configured.

Figure 7:
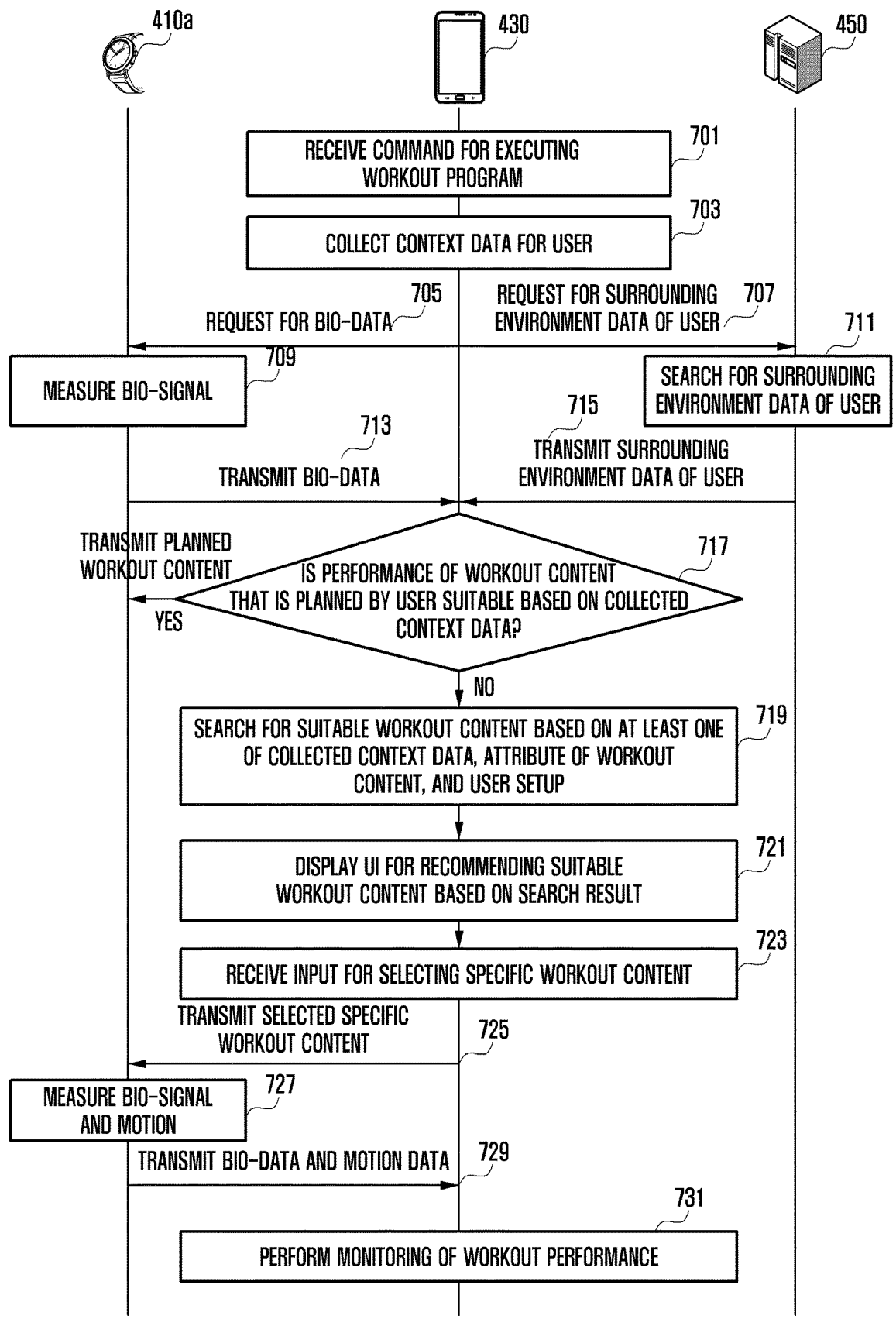
FIG. 7 is a flowchart illustrating an example method of a first system for determining a suitable workout in consideration of a context according to various example embodiments of the present disclosure.

FIG. 7 is a flowchart illustrating an example method of a first system for determining a suitable workout in consideration of a context according to various example embodiments of the present disclosure.

At operation 701, an electronic device 430 may receive a command for executing a workout program. Although not illustrated, the electronic device 430 and a wearable device 410a on a first system, which has received the command for executing the workout program, may perform synchronization. The synchronization may include, for example, an operation in which the wearable device 410a transmits the collected user's bio-data to the electronic device 430 or an operation in which the electronic device 430 updates firmware of the wearable device 410a.

At operation 703, the electronic device 430 may collect context data for the user. According to various embodiments, the electronic device 430 may not only collect the context data that is stored in a memory, but it may also request the context data from an external electronic device.

In order to collect the context data from another external electronic device, the electronic device 430 may transmit a signal for requesting the bio-data to the wearable device 410a at operation 705, and it may transmit a signal for requesting surrounding environment data of a user to a service server 450 of the electronic device 430 at operation 707. Although FIG. 7 illustrates that the context data is simultaneously requested from the wearable device 410a and the service server 450, the context data may be successively requested, and in acquiring the data, it is preferable to preferentially request the data that requires a long period of time.

At operation 709, the wearable device 410a that has received the request for the bio-data from the electronic device 430 may measure the user's bio-data. The wearable device 410a may collect various pieces of bio-information through various sensors.

At operation 711, the service server 450 that has received the request for the surrounding environment data of a user from the electronic device 430 may determine the user location based on a Global Navigation Satellite System (GNSS), and it may search for surrounding environment information based on the determined user location.

The wearable device 410a may transmit at operation 713 the bio data to the electronic device based on the measured bio-signal, and the service server 450 may transmit at operation 715 the surrounding environment data of the user to the electronic device 420 based on the searched surrounding environment information. Although FIG. 7 illustrates that the data is simultaneously transmitted by the wearable device 410a and the service server 450, the data may be successively transmitted, and the device that has acquired the data may preferentially transmit the data regardless of the order.

At operation 717, the electronic device 430 may determine whether the performance of the workout content that is planned by the user is suitable on the basis of the collected context data.

If the electronic device 430 determines at operation 717 that the performance of the planned workout is unsuitable, the process may move to operation 719. At operation 719, the electronic device 430 may search for suitable workout content based on at least one of the collected context data, the attribute of the workout content, and the user setup.

At operation 721, the electronic device 430 may display a UI for recommending the suitable workout content based on the result of the search. The UI for recommending the suitable workout content may be displayed on at least one of the wearable device 410a and the electronic device 430.

At operation 723, the electronic device 430 may receive an input for selecting specific workout content based on the UI for recommending the suitable workout content. The input for selecting the workout content may be performed through the electronic device 430 and the wearable device 410a, and if the wearable device 410a receives the input for the selection, it may further include an operation to transmit the result of the selection to the electronic device 430.

At operation 725, the electronic device 430 transmits the selected specific workout content to the wearable device 410a, and the user performs the specific workout content.

At operation 727, the wearable device 410a may measure the bio-signal in accordance with the specific workout content and may perform motion tracking.

At operation 729, the wearable device 410a may transmit the measured bio-signal and the result of the motion tracking in synchronization with the electronic device 430.

At operation 731, the electronic device 430 may monitor the user's workout performance based on the bio-signal and the motion tracking result, which are transmitted by the synchronized wearable device 410a.

Figure 8:
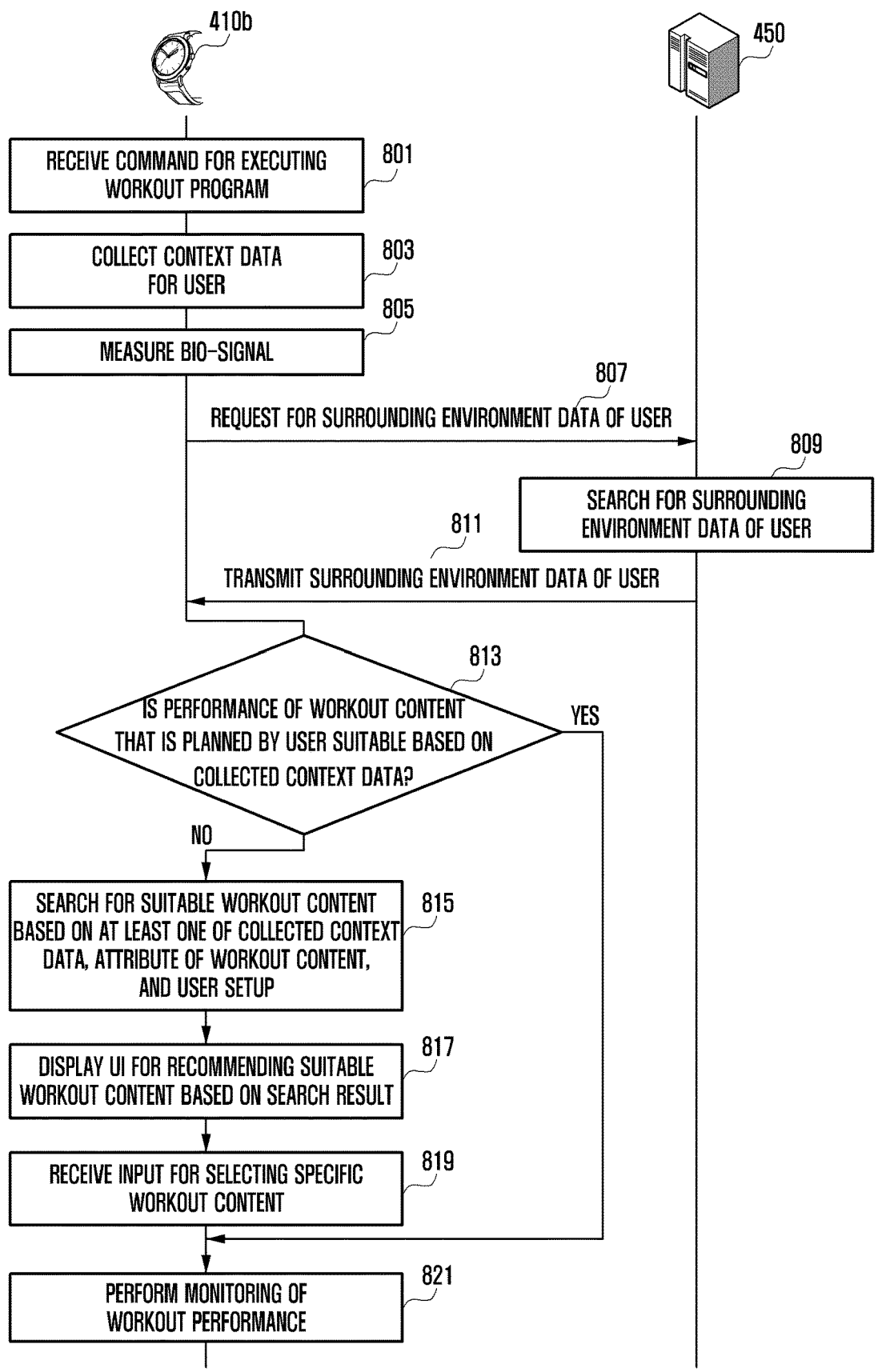
FIG. 8 is a flowchart illustrating an example method of a second system for determining a suitable workout in consideration of a context according to various example embodiments of the present disclosure.

FIG. 8 is a flowchart illustrating an example method of a second system for determining a suitable workout in consideration of a context according to various example embodiments of the present disclosure.

At operation 801, a wearable device 410b may receive a command for executing a workout program.

At operation 803, the wearable device 410b may collect context data for a user. According to various embodiments, the wearable device 410b may not only acquire the user's bio-data using sensors included in the wearable device 410b, but it may also request the context data from an external electronic device in order to collect the context data stored in a memory.

At operation 805, the wearable device 410b may measure the user's bio-signal using at least one sensor included in the wearable device 410b. The measured bio-signal may be converted into bio-data that corresponds to the context data for the user.

In order to collect the context data from another external electronic device, at operation 807, the wearable device 410b may transmit a signal for requesting the surrounding environment data of the user to a service server 450.

At operation 809, the service server 450 that has received the request for the surrounding environment data of the user from the wearable device 410b may determine the user location based on a Global Navigation Satellite System (GNSS), and it may search for surrounding environment information based on the determined user location.

At operation 811, the service server 450 may transmit the surrounding environment data of the user to the wearable device 410b based on the searched surrounding environment information. Although FIG. 8 illustrates that the data is simultaneously transmitted by the wearable device 410b and the service server 450, the data may be successively transmitted, and the device that has acquired the data may preferentially transmit the data regardless of the order.

At operation 813, the wearable device 410b may determine whether the performance of the workout content that is planned by the user is suitable on the basis of the collected context data.

If the wearable device 410b determines that the performance of the planned workout is unsuitable at operation 813, the process may move to operation 815. At operation 815, the wearable device 410b may search for suitable workout content based on at least one of the collected context data, the attribute of the workout content, and the user setup.

At operation 817, the wearable device 410b may display a UI for recommending the suitable workout content based on the result of the search.

At operation 819, the wearable device 410b may receive an input for selecting specific workout content based on the UI for recommending the suitable workout content.

At operation 821, the wearable device 410b may measure the bio-signal and may perform motion tracking in order to monitor the user's workout performance.

FIGS. 9, 10, 11, 12A, 12B, 13A, 13B and 14 are diagrams illustrating a user interface according to various example embodiments of the present disclosure.

Figure 9:

FIG. 9 is a diagram illustrating an example user interface indicating that today's planned workout is running. For example, if it is assumed that today is Wednesday, 2 October and today's planned workout content is running 2.0 km, the user interface may be displayed as illustrated in FIG. 9. Referring to the user interface as illustrated in FIG. 9, it can be known that the user plans to perform brisk walking with a warm-up for 5 minutes, to perform jogging 1 km (or for 8 minutes), and to perform walking 0.5 km (or for 5 minutes).

The electronic device may determine whether the performance of today's planned workout content as illustrated in FIG. 9 is suitable; and, if the result of the determination is that it is suitable, the user interface as illustrated in FIG. 9 may be displayed.

Figure 10:
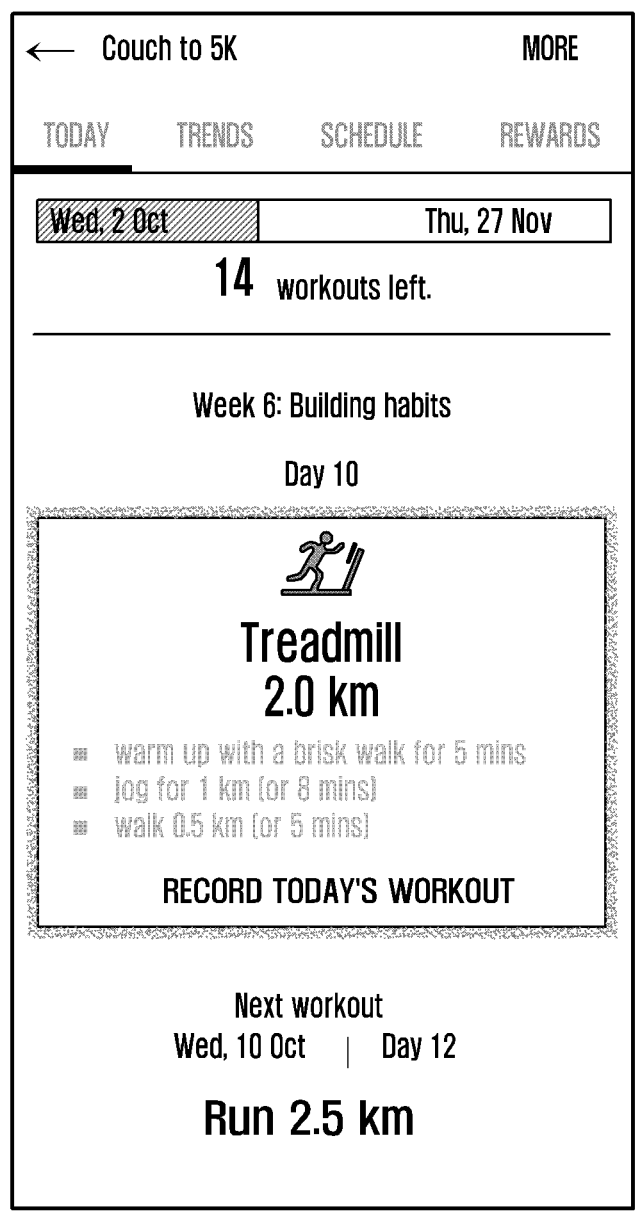
Figure 11:
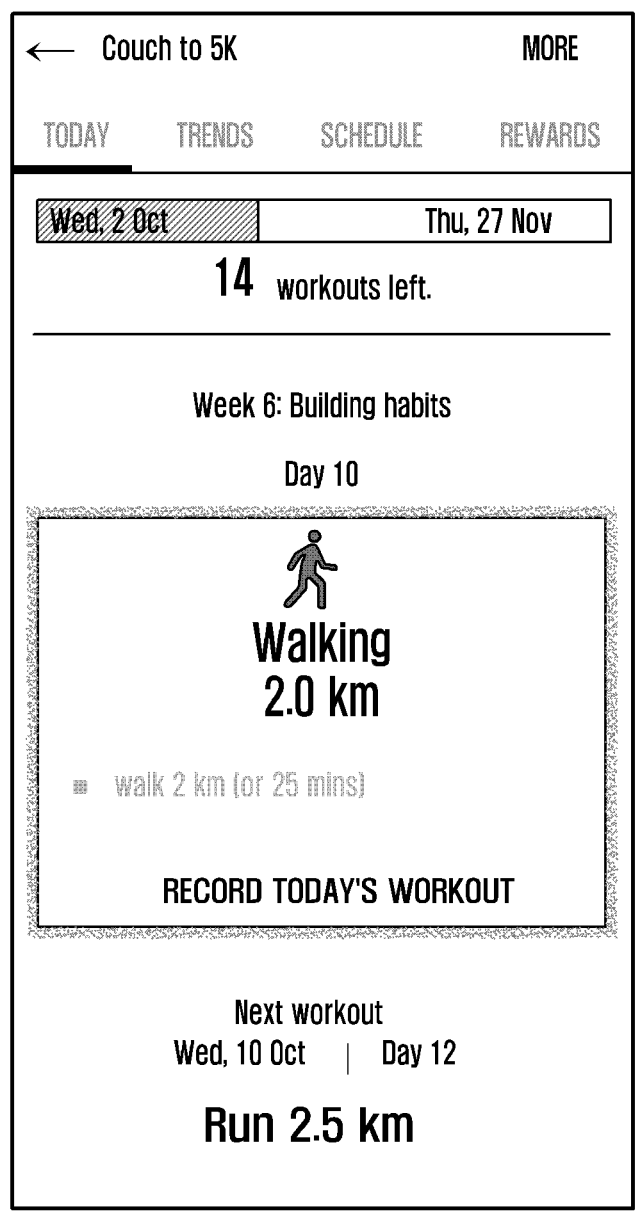

FIGS. 10 and 11 are diagrams illustrating example user interfaces indicating that the performance of running that is planned by the user as illustrated in FIG. 9 is unsuitable and a substitute workout is performed.

For example, the electronic device may determine that today's planned outdoor workout is unsuitable with reference to environment-based context data. For example, if the environment-based context data corresponds to 90% probability of rainfall, very bad fine dust concentration, high ultraviolet index, or high asthma-pulmonary disease possibility index, the electronic device may determine that it is unsuitable to perform the outdoor workout. In this case, the electronic device may search for indoor workout content in consideration of collected context data, an attribute of the workout content, and user setup. FIG. 10 illustrates the user interface indicating that the electronic device determines that today's planned outdoor workout is unsuitable and substitute workout content is displayed. For example, if the result of the determination of the electronic device is that the user's condition and workout strength, but not the user surrounding environment, are suitable, the electronic device may recommend treadmill that is workout content having a strength that is similar to the strength of the previously planned running. Further, in the same manner as performance of the previously planned workout as illustrated in FIG. 9, the user may plan to perform brisk walking with warm-up for 5 minutes, to perform jogging 1 km (or for 8 minutes), and to perform walking 0.5 km (or for 5 minutes).

In another embodiment, the electronic device may determine that the strength of today's planned workout is unsuitable with reference to the user-based context data. For example, if today is in the user's menstrual cycle, if an average sleep time for latest 7 days is less than 7 hours, if planned workout content has already been performed, or if calorie consumption on the day is measured high, the electronic device may determine that the user's condition is unsuitable for performing today's planned workout. In this case, the electronic device may search for workout content that is suitable for the user's condition in consideration of the collected context data, the attribute of the workout content, and the user setup. FIG. 11 illustrates the user interface indicating that the electronic device determines that the user's condition is unsuitable for performing today's planned workout content and substitute workout content is displayed. For example, if the user's surrounding environment is suitable for performing an outdoor workout, but the user's condition is unsuitable for performing the workout having high strength, the electronic device may recommend walking that is workout content having a weak strength instead of the previously planned running. Further, the plan may be changed to perform walking only by the entire omission of the previously planned brisk walking and jogging.

Figure 12B:
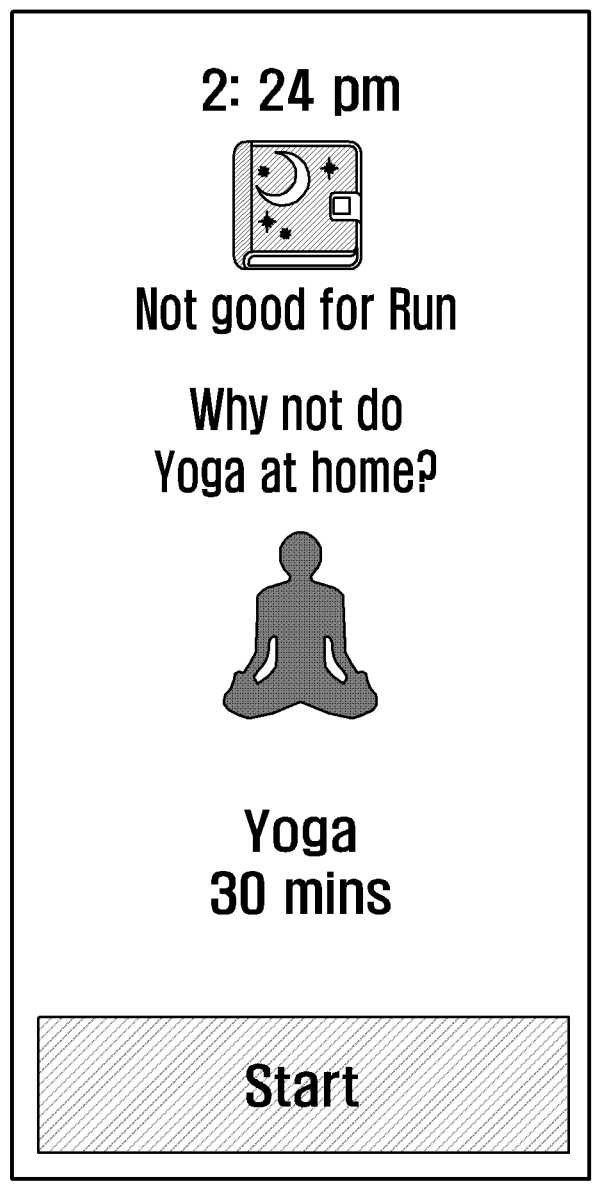

FIGS. 12A and 12B are diagrams illustrating example user interfaces indicating that the performance of running content that is planned by the user as illustrated in FIG. 9 is unsuitable and a substitute workout is recommended. The user interfaces illustrated in FIGS. 12A and 12B recommend one piece of workout content, but they are not limited thereto. The user interfaces may recommend plural pieces of workout content.

The user interface of FIG. 12A displays a rain icon; thus, the user can intuitively recognize that the performance of an outdoor workout having a high strength is unsuitable. Further, the electronic device determines that running is unsuitable in consideration of the user's condition and workout strength and thus recommends performing stretching at home.

The user interface of FIG. 12B displays a menstrual cycle icon; thus, the user can intuitively recognize that the performance of a workout having a high strength is unsuitable. Further, the electronic device determines that performance of workout content having a high strength is unsuitable in consideration of various kinds of context data and thus recommends doing yoga at home.

Figure 13A:
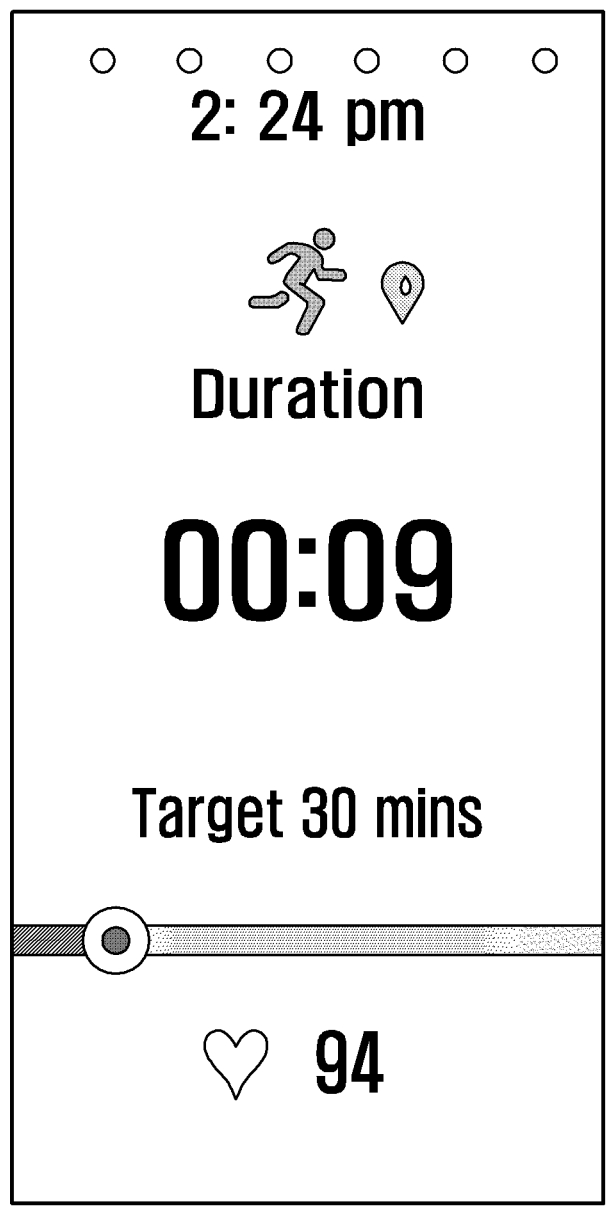
Figure 13B:
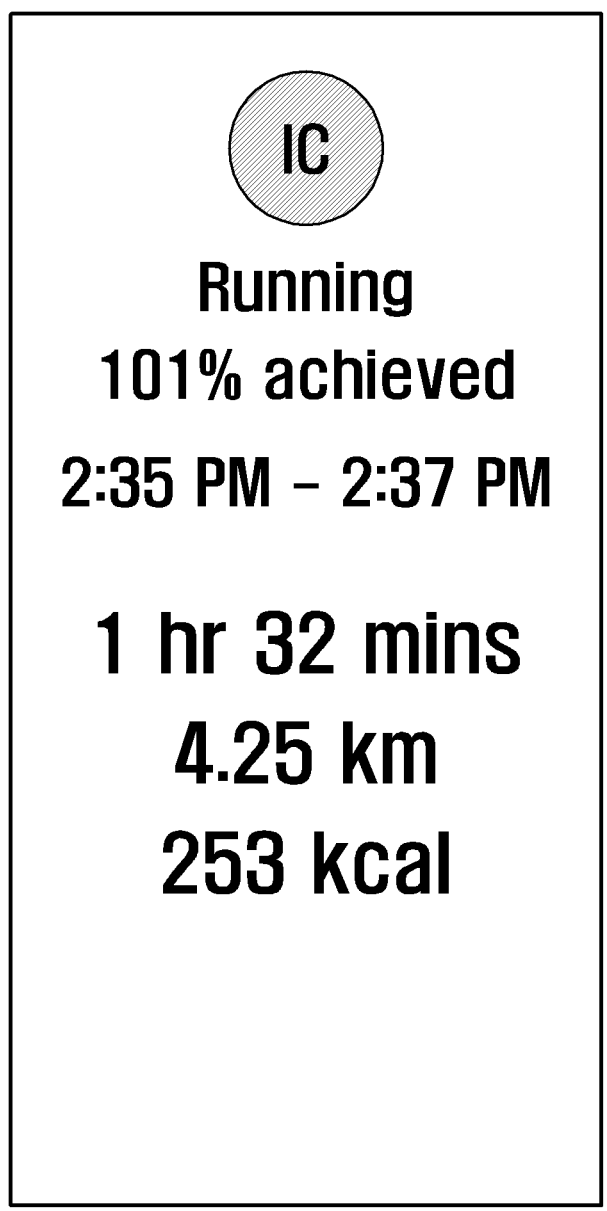

FIGS. 13A and 13B are diagrams illustrating example user interfaces for monitoring a user's workout performance.

Referring to FIG. 13A, the user interface may display a workout performance time and a target workout time together with an icon that enables the user to intuitively confirm the workout content that is currently being performed by the user. For example, the user interface may also display, in real time, the current user's bio-data that is measured by a wearable device. For example, FIG. 13A illustrates a heart rate.

Referring to FIG. 13B, the user interface may display a record of workout content that the user has currently completed. For example, the currently performed workout content, the target attainment rate, the performance time, and other records can be displayed together.

Figure 14:

FIG. 14 is a diagram illustrating an example user interface in the case where performance of planned workout content or suitably changed workout content has been completed according to an example embodiment.

Referring to FIG. 14, the user interface may display workout content performance and target attainment, and it may further display a workout target for this week and the next planned workout content.

Although not illustrated, in the case where the user performs a changed workout content according to various embodiments of the present disclosure, future workout plans may also be changed. For example, if a part of plans that are established according to the workout target for one week is changed, the remaining plans should be changed together to reach the workout target. For example, it is assumed that the workout target for this week is consumption of 1000 Kcal, and today's workout content to consume 150 Kcal is planned. According to various embodiments of the present disclosure, the electronic device may determine that it is unsuitable for the user to perform today's planned workout content. Accordingly, the electronic device may recommend workout content having a strength that is weaker than the strength of the today's planned workout content. In this case, the workout content having the weak strength consumes calories that are lower than the calories of the pre-planned workout content; thus, the electronic device may change the future plans to reach the target value.

The various example embodiments of the present disclosure are merely provided to assist in a comprehensive understanding of the disclosure and not suggestive of limitation. Therefore, it should be understood that many variations and modifications of the basic concept herein described will still fall within the spirit and scope of the disclosure as defined in the appended claims.

What is claimed is:
1. An electronic device comprising:
a communication module comprising communication circuitry configured to communicate with at least one other electronic device;
a display;

a processor electrically connected to the communication module and the display; and a memory electrically connected to the processor and storing instructions therein, wherein the instructions, when executed by the processor, cause the processor to:

receive a command for executing an application including a plurality of workout contents, acquire user information including at least one of a user's workout purpose or a user's workout style, receive a user's bio-data from at least one wearable device, and receive surrounding environment data of the user from a server, identify whether at least one of the user information, the user's bio-data, or the surrounding environment data of the user corresponds to attribute information of a first workout content comprising at least one of a performance place, strength, or workout purpose of the first workout content, the first workout content being workout content pre-planned by the user among the plurality of workout contents, in response to at least one of the user information, the user's biometric data, or the surrounding environment data not corresponding to the attribute information of the first workout content, search for a second workout content having attribute information corresponding to the user information, the user's bio-data, and the surrounding environment information in the plurality of workout contents, the searched second workout content being different from the first workout content, display a user interface including the pre-planned first workout content and the searched second workout content, and display, in response to detecting user input for selecting one of the pre-planned first workout content and the searched second workout content, the selected workout content.

2. The electronic device of claim 1, wherein the instructions further include instructions which, when executed, cause the processor to control the display to display a user interface for recommending the second workout content based on the result of the search.

3. The electronic device of claim 1, wherein the instructions further include instructions which, when executed, cause the processor to receive at least one of a cough possibility index, an asthma-pulmonary disease possibility index, a stroke possibility index, or a skin disease possibility index from the server.

4. The electronic device of claim 1, wherein the user information further comprises personal record data.

5. The electronic device of claim 1, wherein the surrounding environment data comprises at least one of: a user's surrounding weather, humidity, fine dust concentration, an atmospheric temperature, a wind direction, a wind speed, an altitude, ultraviolet rays, a rainfall probability, a rainfall amount, and a wave height.

6. A wearable device comprising:

a communication module comprising communication circuitry configured to communicate with at least one other electronic device;

a display;

a sensor module comprising at least one sensor configured to measure a bio-signal;

a processor electrically connected to the communication module, the display, and the sensor module; and a memory electrically connected to the processor and storing instructions therein, wherein the instructions, when executed by the processor, cause the processor to:

receive a command for executing an application including a plurality of workout contents, acquire user information including at least one of a user's workout purpose or a user's workout style based on user input, receive surrounding environment data of a user from a server, control the sensor module to measure a user's bio-data, identify whether at least one of the user information, the user's bio-data, or the surrounding environment data of the user corresponds to attribute information of a first workout content comprising at least one of a performance place, strength, or workout purpose of the first workout content, the first workout content being workout content pre-planned by the user among the plurality of workout contents, in response to at least one of the user information, the user's biometric data, or the surrounding environment data not corresponding to the attribute information of the first workout content, search for a second workout content having attribute information corresponding to the user information, the user's bio-data, and the surrounding environment information in the plurality of workout contents, the searched second workout content being different from the first workout content, display a user interface including the pre-planned first workout content and the searched second workout content, and display, in response to detecting user input for selecting one of the pre-planned first workout content and the searched second workout content, the selected workout content.

7. The wearable device of claim 6, wherein the instructions further include instructions which, when executed, cause the processor to control the display to display a user interface for recommending the second workout content based on the result of the search.

8. A method for determining a workout in consideration of a context, the method comprising:

receiving a command for executing an application including a plurality of workout contents;

acquiring user information including at least one of a user's workout purpose or a user's workout style based on user input;

receiving a user's bio-data from at least one wearable device, and receiving surrounding environment data of a user from a server;

identifying whether at least one of the user information, the user's bio-data, or the surrounding environment data of the user corresponds to attribute information of a first workout content comprising at least one of a performance place, strength, or workout purpose of the first workout content, the first workout content being workout content pre-planned by the user among the plurality of workout contents;

in response to at least one of the user information, the user's biometric information, or the surrounding environment information not corresponding to the attribute information of the first workout content, searching for a second workout content having attribute information corresponding to the user information, the user's bio-data, and the surrounding environment information in the plurality of workout contents, the searched second workout content being different from the first workout content, displaying a user interface including the pre-planned first workout content and the searched second workout content, and displaying, in response to detecting user input for selecting one of the pre-planned first workout content and the searched second workout content, the selected workout content.

9. The method of claim 8, further comprising displaying a user interface for recommending the second workout content based on the result of the search.

\* \* \* \* \*